United States Patent [19]

Miyagawa

[11] Patent Number: 5,419,334
[45] Date of Patent: May 30, 1995

[54] ULTRASONIC PROBE
[75] Inventor: Toyomi Miyagawa, Chigasaki, Japan
[73] Assignee: Kabushiki Kaisha Toshiba, Kawasaki, Japan
[21] Appl. No.: 186,420
[22] Filed: Jan. 28, 1994
[30] Foreign Application Priority Data
  Jan. 29, 1993 [JP] Japan .................................. 5-013413
[51] Int. Cl.$^6$ .............................................. A61B 8/12
[52] U.S. Cl. .............................................. 128/662.06
[58] Field of Search ....................... 128/660.01, 660.09, 128/660.10, 662.06

[56] References Cited
U.S. PATENT DOCUMENTS

| | | | |
|---|---|---|---|
| 4,391,282 | 7/1983 | Ando et al. | 128/660.10 |
| 4,887,605 | 12/1989 | Angelsen et al. | 128/662.06 |
| 5,020,539 | 6/1991 | Yokoi et al. | 128/662.06 |
| 5,181,514 | 1/1993 | Solomon et al. | 128/662.06 |

FOREIGN PATENT DOCUMENTS
  62-7301 2/1987 Japan .

*Primary Examiner*—George Manuel
*Attorney, Agent, or Firm*—Foley & Lardner

[57] ABSTRACT

An ultrasonic probe for observing an object by emitting an ultrasonic wave to the object and detecting another ultrasonic wave reflected from the object comprises: a flexible tube; an ultrasonic transducer disposed within the tube rotatably about an axial center of the tube; and a rotational information detecting apparatus for detecting rotational information of the ultrasonic transducer which includes: a signal generating surface disposed in the tube coaxially with respect to the axial center of the tube and having reflecting portions and non-reflecting portions formed alternately and repeatedly; at least one optical fiber arranged along and near the axial center of the tube, for guiding a light beam to be irradiated upon the signal generating surface from an end surface of the optical fiber and for receiving and guiding an optical signal reflected from the signal generating surface at the end surface thereof; and an optical signal detecting section for detecting the rotational information on the basis of the optical signal guided through the optical fiber. Since the optical fiber for guiding a light beam to be irradiated upon the signal generating surface and further the optical signal reflected from the signal generating surface is disposed in the vicinity of the axial center of the tube, even when the ultrasonic probe is bent, it is possible to reduce the expansion and contraction rate of the optical fiber to such a small range as with the case where the optical fiber is bent at the axial center, thus preventing the optical fiber from being damaged or cut off and improving the transmission characteristics of the optical fiber.

12 Claims, 4 Drawing Sheets

ULTRASONIC PROBE

BACKGROUND OF THE INVENTION

1. Field of the Invention

The present invention relates to an ultrasonic probe used for an ultrasonic diagnosis apparatus inserted into a body cavity to observe an internal organ, and in particular to an ultrasonic probe for detecting and transmitting rotational information of an ultrasonic transducer disposed in a tubular member rotatably about an axis thereof through an optical fiber.

2. Description of the Prior Art

As the ultrasonic diagnosis apparatus inserted into a body cavity for observation of the motion or the texture of an internal organ, an ultrasonic probe of mechanical scanning type is so far known, in Japanese Published and Examined Utility Model Application No. 62-7301, for instance.

FIG. 1 is a cross-sectional view showing the conventional ultrasonic probe. In the drawing, an ultrasonic transducer 3 fitted to an ultrasonic scanning member 2 is disposed in an end portion of a flexible cylindrical casing 1. The ultrasonic scanning member 2 is fitted to a rotary axle 4 disposed at an axial center of the cylindrical casing 1 so as to be rotatable together with the rotary axle 4 in the cylindrical casing 1.

Further, a disk 6 having a signal generating surface 5 on which reflecting portions and non-reflecting portions are formed alternately and repeatedly is fixed to this rotary axle 4. The disk 6 rotates together with the rotary axle 4 and therefore together with the ultrasonic transducer 3.

Further, a light emitting optical fiber 7 and a light receiving optical fiber 8 are both arranged along the rotary axle 4 in the vicinity of the inner circumferential surface of the cylindrical casing 1.

The disk 6, the light emitting optical fiber 7 and the light receiving optical fiber 8 constitute a rotational information detecting apparatus for detecting rotational information of the rotary axle 4 such as rotational angles and rotational angular velocity of the rotary axle 4.

On the other hand, an ultrasonic drive signal for driving the ultrasonic transducer 3 and a received ultrasonic signal reflected from a body cavity 10 are transmitted through a signal cable 9 arranged in the rotary axle 4.

In operation, when the ultrasonic probe is inserted into a body cavity, the motion or the texture of the internal organ can be observed by rotating the ultrasonic transducer 3. Here, the ultrasonic transducer 3 is rotated via the ultrasonic scanning member 2 rotated by the rotary axle 4 driven by a motor (not shown).

A light beam is emitted from an end of the light emitting optical fiber 7 to the signal generating surface 5. Since the reflecting portions and the non-reflecting portions are formed alternately and repeatedly on the signal generating surface 5, when the disk 6 rotates, a light beam emitted from the light emitting optical fiber 7 is reflected from the signal generating surface 5 as an optical signal. Here, the optical signal received by an end of the light receiving optical fiber 8 changes in light intensity with respect to time, so that it is possible to detect the rotational information (e.g., the rotational angle and the rotational angular velocity) of the rotary axle on the basis of the received optical signal.

An output terminal of the light receiving optical fiber 8 is connected to a control section of the motor for driving the rotary axle 4. The rotational information detecting apparatus and the control section of the motor for driving the rotary axle 4 are connected so as to form a closed loop, so that the rotational angle and the angular velocity of the rotary axle 4 can be controlled on the basis of the rotational information.

However, the conventional ultrasonic probe involves the following problems:

The optical fiber bundle composed of the light emitting optical fiber 7 and the light receiving optical fiber 8 is arranged in the vicinity of the inner circumferential surface of the cylindrical casing 1; that is, the optical fiber bundle is positioned radially outward away from the rotary axle 4. Therefore, when the ultrasonic probe is inserted into a curved body cavity 10 as shown in FIG. 2, the rate of expansion and contraction of the optical fibers 7 and 8 differs largely according to the curvature direction of the optical fiber bundle, so that there exists a problem in that the optical fibers are damaged or cut off because the expansion and contraction rate of the optical fiber exceeds its allowable range according to the curvature direction.

In addition, since the optical fibers are arranged in the vicinity of the inner circumferential surface of the cylindrical casing 1, the expansion and contraction rate of the optical fibers 7 and 8 is larger than that of the cylindrical casing 1 at its axial center. Therefore, there exists another problem in that the transmission characteristics of the optical signal are subjected to change due to a large distortion generated in the optical fiber, thus it has been difficult to obtain an accurate rotational information of the rotary axle 4.

SUMMARY OF THE INVENTION

With these problems in mind, therefore, it is the object of the present invention to provide a high reliable ultrasonic probe, by which it is possible to obtain accurate rotational information for controlling the rotational motion of the ultrasonic transducer, while preventing the optical fiber from being damaged or cut off.

To achieve the above-mentioned object, an ultrasonic probe for observing an object to be observed by emitting an ultrasonic wave to the object and detecting another ultrasonic wave reflected from the object according to the present invention, which comprises: a flexible tube; an ultrasonic transducer disposed within said tube rotatably about an axial center of said tube; and a rotational information detecting apparatus for detecting rotational information of said ultrasonic transducer, including: signal generating means disposed within said tube coaxially with respect to the axial center of said tube and having reflecting portions and non-reflecting portions formed alternately and repeatedly; at least one optical fiber arranged along and in the vicinity of the axial center of said tube, for guiding a light beam to be irradiated upon said signal generating means from an end surface of said optical fiber and for receiving and guiding an optical signal reflected from said signal generating means at the end surface thereof; and optical signal detecting means for detecting the rotational information on the basis of the optical signal guided through said optical fiber.

In the first embodiment of the present invention, the signal generating means is formed on a disk disposed coaxially with said tube, and the end surface of said optical fiber is guided radially outward away from the vicinity of the axial center of said tube so as to be opposed to said signal generating means.

Further, in the second embodiment of the present invention, the signal generating means is formed on an inner surface of a cylinder disposed coaxially with said tube, and a reflecting mirror is disposed at a position opposite to the end surface of said optical fiber so as to be rotatable together with said optical fiber, for emitting the light beam to said signal generating means and receiving the optical signal reflected therefrom.

Further, in the third embodiment of the present invention, the signal generating means is formed on an inner surface of a cylinder disposed coaxially with said tube, and said optical fiber is bent in the vicinity of the axial center of said tube in such a way that the end surface of said optical fiber is opposed to said signal generating means.

Further, in any embodiments of the present invention, the light beam and the optical signal are both guided through said same optical fiber. The optical signal detecting means detects the optical signal by separating polarized light of the optical signal from polarized light of the light beam.

In the ultrasonic probe according to the present invention, since the optical fiber for guiding a light beam to be irradiated upon the signal generating surface and further the optical signal reflected from the signal generating surface is disposed in the vicinity of the axial center of the tube, even when the ultrasonic tube is bent, it is possible to reduce the expansion and contraction rate of the optical fiber to such a small range as with the case where the optical fiber is bent at the axial center, so that the optical fiber can be prevented from being damaged or cut off and further the transmission characteristics of the optical fiber can be improved in order to obtain accurate rotational information of the ultrasonic transducer.

DETAILED DESCRIPTION OF THE PREFERRED EMBODIMENTS

The first embodiment of the ultrasonic probe according to the present invention will be described in detail hereinbelow with reference to the attached drawings.

Figure 1:
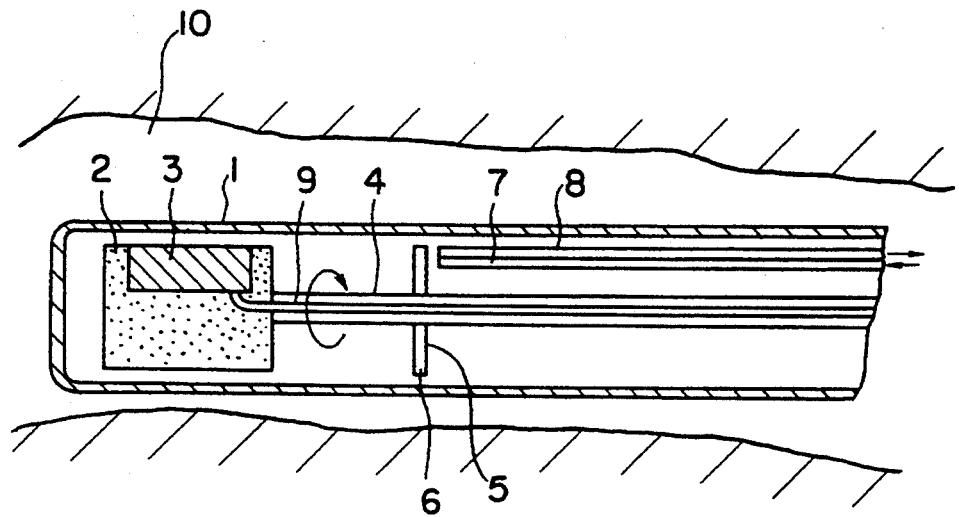
FIG. 1 is a cross-sectional view showing an end portion of a conventional ultrasonic probe.
Figure 2:
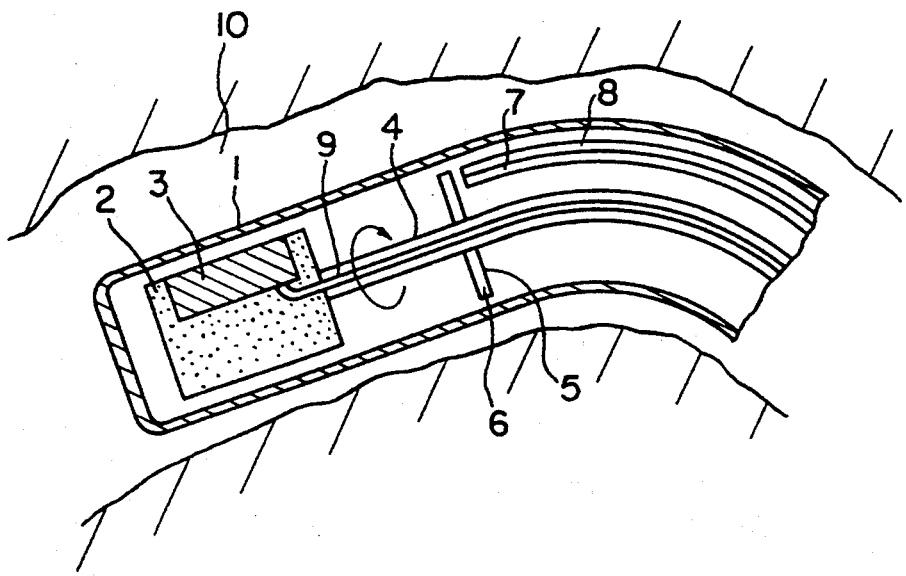
FIG. 2 is a cross-sectional view showing the conventional ultrasonic probe inserted into a curved body cavity.
Figure 3:
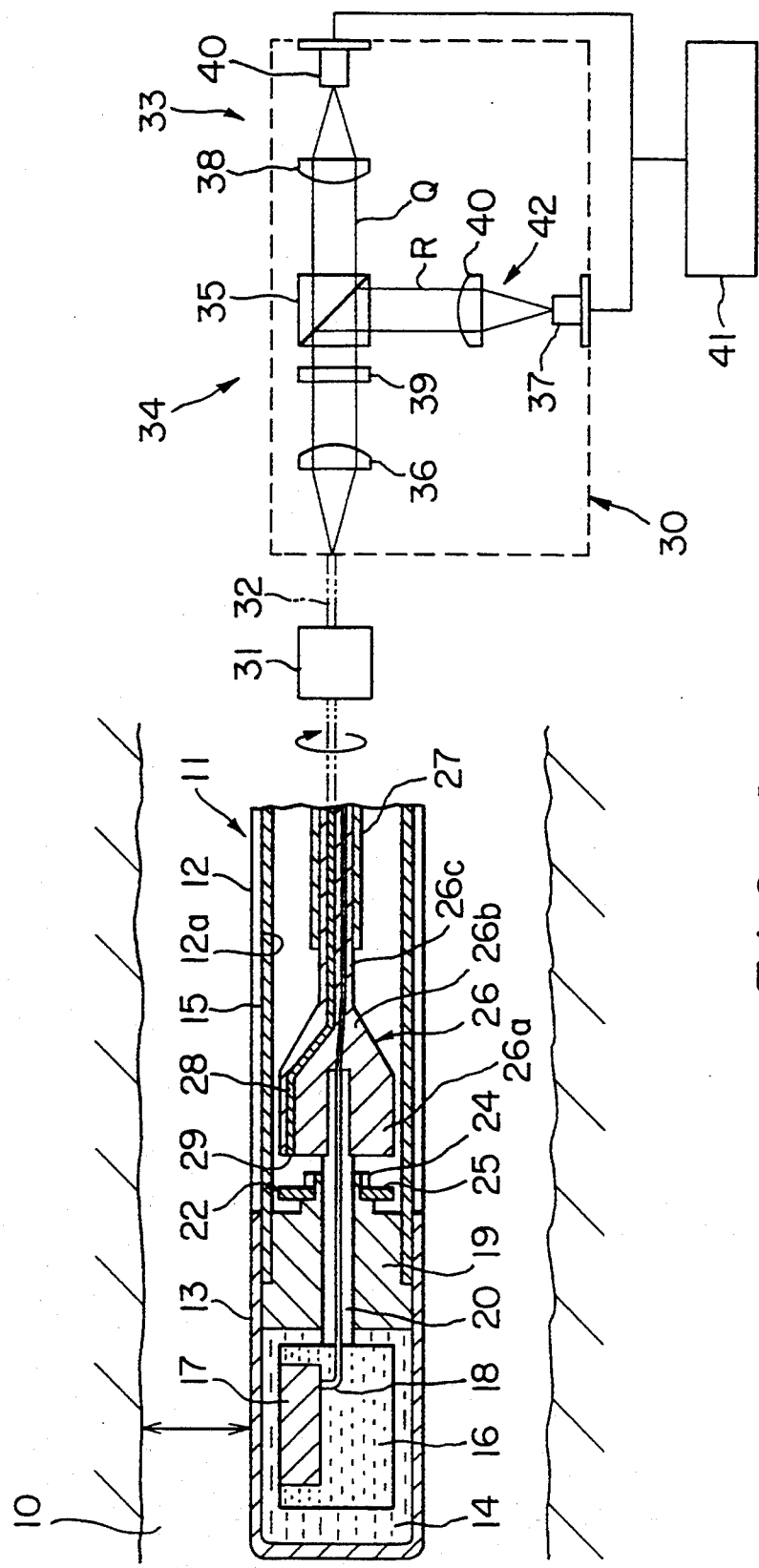
FIG. 3 is a cross-sectional view showing an end portion of a first embodiment of the ultrasonic probe, together with a diagrammatical view showing the light emitting and receiving apparatus according to the present invention.

In FIG. 3, an end portion 11 of the ultrasonic probe is inserted into a tubular body cavity 10. A cap 13 is fixed to an end of a flexible tube 12 which constitutes the end portion 11 of the ultrasonic probe. The cap 13 is formed of a material having a property for transmitting an ultrasonic wave. An ultrasonic transducer housing 14 for accommodating an ultrasonic transducer 17 is formed within the cap 13. The ultrasonic transducer housing 14 is filled with an ultrasonic propagation medium. Further, within the ultrasonic transducer housing 14, an ultrasonic scanning member 16 is disposed.

The ultrasonic transducer 17 is fixed to the side surface of the ultrasonic scanning member 16. The ultrasonic transducer 17 is composed of a generating section for generating a high frequency ultrasonic wave of several tens of MHz and a receiving section for receiving another ultrasonic wave reflected from an inner wall of a tubular body cavity 10. The ultrasonic transducer 17 is connected to a transmission cable 18 through which a drive signal for driving the ultrasonic transducer 17 and a receive signal indicative of the reflected ultrasonic wave are transmitted.

A bearing 19 is fitted to a cylindrical liner tube 15 fitted to an inner wall 12a of the tube 12. A rotary axle 20 located at the axial center of the tube 12 is rotatably supported by the bearing 19. One end of the rotary axle 20 is fixed to the ultrasonic scanning member 16, and the other end of the rotary axle 20 is connected to one end of an optical fiber scanning member 26. The other end of the optical scanning member 26 is fitted to an inner end portion of a flexible axle 27 formed of a flexible material. Further, the other end of the flexible axle 27 extends to an entrance end of the ultrasonic probe so as to be connected to a motor rotary shaft (not shown).

The optical fiber scanning member 26 is formed with a large-diameter cylindrical portion 26a at one end thereof, a conical portion 26b connected to the cylindrical portion 26a, and a small-diameter cylindrical portion 26c at the other end thereof which extends toward the entrance end of the ultrasonic probe.

Further, a disk 22 for constituting an encoder is located at the axial center of the tube 12 and fixed to an end portion of the bearing 19 by a socket 24 in such a way as to be opposed to an end surface of the optical fiber scanning member 26. Therefore, the disk 22 is not rotated together with the rotary axle 20.

Figure 4A:
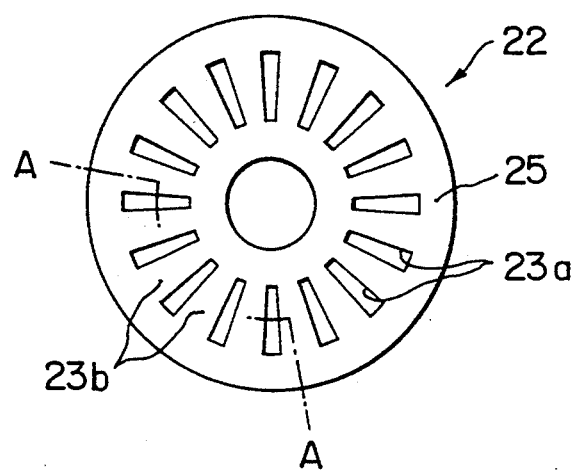
FIG. 4(a) is a plane view showing a disk having a signal generating surface on which reflecting portions and non-reflecting portions are arranged alternately and repeatedly.
Figure 4B:
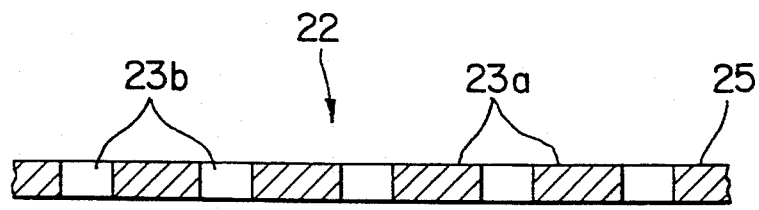
FIG. 4(b) is a cross-sectional view showing the same disk, taken along the line A—A shown in FIG. 4(a)

As depicted in FIGS. 4(a) and (b), the disk 22 has a signal generating surface 25 on which reflection portions 23a and non-reflection portions 23b are formed alternately and repeatedly. The reflection portions 23a are formed by vaporizing a high-reflection power material (e.g., chromium) onto a glass plate material, for instance.

In the vicinity of the axial center of the tube 12, an optical fiber 28 is disposed along the axial center of the tube 12. That is, the optical fiber 28 is arranged along the axial center within a range near the axial center, which is radially inward away from the inner wall 12a of the tube 12.

One end of the optical fiber 28 is connected to an optical coupler 31 at the entrance end of the ultrasonic probe. The other end of the optical fiber 28 extends to an end surface of the optical fiber scanning member 26, being passed through the flexible axle 27 and the small-diameter cylindrical portion 26c of the optical fiber scanning member 26 and further being guided along the outer periphery of the conical portion 28b and the large-diameter cylindrical portion 28c of the optical fiber scanning member 28. An inner end surface 29 of the optical fiber 28 is guided so as to be radially apart from the vicinity of the axial center and to be opposed to the signal generating surface 25 in parallel thereto.

The optical fiber 28 is composed of at least one optical fiber and used in common as a light emitting optical fiber and a light receiving optical fiber.

The optical coupler 31 is connected to a light emitting and receiving apparatus 30 via another optical fiber 32. The optical coupler 31 connects the rotatably supported optical fiber 28 of the probe and the fixedly supported optical fiber 32 optically.

The light emitting and receiving apparatus 30 is composed of a light emitter 33 for generating a parallel beam, a light separator 34 for splitting or polarizing the light, and a light receiver 42 for detecting an optical signal.

The light emitter 33 includes a light source 40 and a lens 38 for converting light emitted from the light source 40 into a parallel beam Q. The light separator 34 includes a light splitting element 35 for splitting the parallel beam passed through the lens 38, and a light polarizing element 39 for providing a phase difference to the splitted beam.

The light separator 34 separates the light irradiated upon the signal generating surface 25 from the light (optical signal) reflected by the signal generating surface 25 or vice versa. The light polarizing element 39 converts the linearly polarized light into the circularly polarized light. After the parallel beam Q has been passed through the optical splitting element 35, only the light polarized into the linearly polarized light is guided to the light polarizing element 39. Further, the light converted from the linearly polarized light into the circularly polarized light through the light polarizing element 39 is guided into the optical fiber 32 through another lens 36.

As described above, the light emitted from the light emitter 33 is passed through the light separator 34, guided into the optical fiber 32, passed through the optical coupler 31, transmitted into the optical fiber 28, and then irradiated upon the signal generating surface 25 through the end surface 29 of the optical fiber 28.

The polarized light of the optical signal reflected by the signal generating surface 25 is the circularly polarized light. This optical signal is allowed to be incident upon the optical fiber 28 again through the end surface 29 thereof, transmitted through the optical coupler 31, the optical fiber 32, etc., and then converted into the linearly polarized light through the light polarizing element 39. Since this linearly polarized light is perpendicular in direction to the linearly polarized light initially passed through the lens 38 and then through the light splitting element 35, this optical signal is not passed through the light splitting element 35 toward the light source 40, but reflected by the light splitting element 35 as a parallel beam R. The splitted parallel beam R is focused onto an optical signal detecting element 37 through another lens 40. The optical signal detecting element 37 detects the intensities of the light reflected by the reflecting portions 23a and the non-reflecting portions 23b.

The light source 40 and the optical signal detecting element 37 are both connected to a control circuit section 41. The control circuit section 41 standardizes the intensity of the optical signal detected by the optical signal detecting element 37 on the basis of the light intensity of the light source 40, calculates the rotational information such as the rotational angle and the rotational velocity of the rotary axle 20, and forms an image on the basis of the signals transmitted through the signal cable 18 and these calculated rotational information.

The practical dimensions of the ultrasonic probe is about 2 to 3 mm in outer diameter of the tube 12 and about 2 m in total length.

The functional operation of the first embodiment according to the present invention will be described hereinbelow.

When the flexible axle 27 is rotated by the motor, the optical fiber scanning member 26, the rotary axle 20, the ultrasonic scanning member 16 and the ultrasonic transducer 17 are all rotated. Since the disk 22 is fixed to the bearing 19, the light beam emitted from the end surface 29 of the optical fiber 28 is irradiated upon the signal generating surface 25 being rotated around the axis of the tube 12. Since the signal generating surface 25 is formed with the reflecting portions 23a and the non-reflecting portions 23b, respectively, the intensity of the optical signal reflected by the signal generating surface 25 changes with respect to time according to the rotational speed of the rotary axle 20. The optical signal thus obtained is separated through the light separator 34 from the light source 40 to the parallel beam R, detected by the optical signal detecting element 37, and then calculated by the control circuit section 41 to obtain the rotational information such as the rotational angle and the rotational velocity of the rotary axle 20.

As described above, in the construction of the ultrasonic probe according to the present invention, since the optical fiber 28 is arranged in the vicinity of and along the axial center of the tube 12, even when the ultrasonic probe is inserted into a body cavity under bending condition, it is possible to limit the expansion and contraction rate of the optical fiber 28 within an extremely small range roughly the same as with the case where the optical fiber 28 is located at the axial center of the tube 12, with the result that it is possible to prevent the optical fiber 28 from being damaged or cut off.

In addition, even if the ultrasonic probe is bent, since the optical fiber 28 can be expanded and contracted within an extremely small range, it is possible to obtain accurate rotational information, without generating a large distortion of the optical fiber and without changing the transmission characteristics of the optical signal.

Further, since the optical fiber 28 is used in common for the light emitting optical fiber and the light receiving optical fiber, it has become possible to use only a single optical fiber. Accordingly, the optical fiber 28 can be arranged in the further close vicinity of the axial center of the tube 12, so that when the ultrasonic probe is bent, it is possible to reduce the expansion and contraction rate of the optical fiber 28 within a further small limited range.

Further, since the fiber scanning member 26 is formed with the conical portion 26b and the large-diameter cylindrical portion 28a, the end surface 29 of the optical fiber 28 can be located radially outward away from the vicinity of the axial center of the tube 12 at only the position facing the signal generating surface 25, with the result that it is possible to detect rotational information at a high precision.

Further, in the above-mentioned embodiment, the disk 22 is fixed and the optical fiber 28 is rotated around the axial center of the tube 12. Without being limited thereto, however, the present invention can be applied to the case where the disk 22 is rotated together with the rotary axle 20 under the condition that the optical fiber 28 is fixed.

Figure 5:
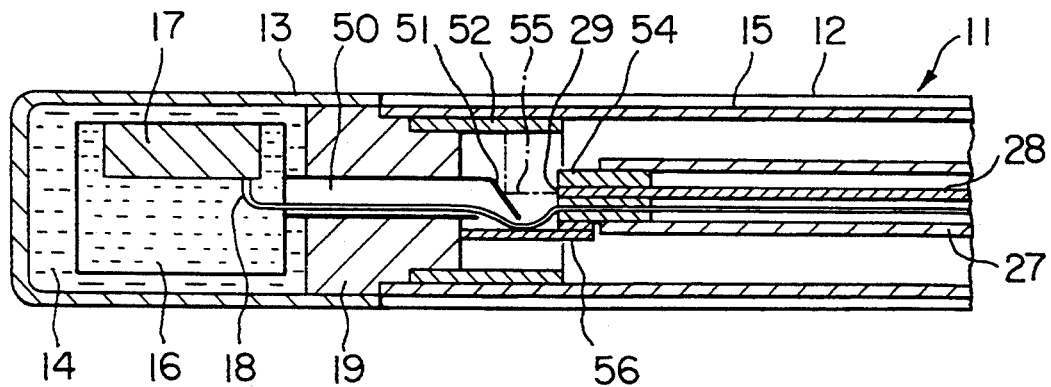
FIG. 5 is a cross-sectional view showing the end portion of a second embodiment of the ultrasonic probe according to the present invention.

A second embodiment of the present invention will be described hereinbelow with reference to FIG. 5.

In this embodiment, the optical fiber 28 is disposed so as to be passed through the flexible axle 27 and an optical fiber scanning member 54 attached to the end of the flexible axle 27. The end surface 29 of the optical fiber 28 reaches the end surface of the optical fiber scanning member 54. A rotary axle 50 is located at the axial center of the tube 12, and rotatably supported by the bearing 19. The one end of the rotary axle 50 is fixed to the ultrasonic scanning member 16. A plane reflecting mirror 51 is attached to the other end of the rotary axle 50 at an inclination angle of about 45 degrees with respect to the axial center of the tube 12 so as to be opposed to the end surface 29 of the optical fiber 28. The transmission cable 18 is arranged in such a way as to be guided from the ultrasonic transducer 17 to the interior of the rotary axle 50 through the side portion of the rotary axle 50. The optical fiber scanning member 54 and the rotary axle 50 are connected with each other by a connection body 56 so that the optical fiber 28 can be rotated together with the rotary axle 50.

Figure 6:
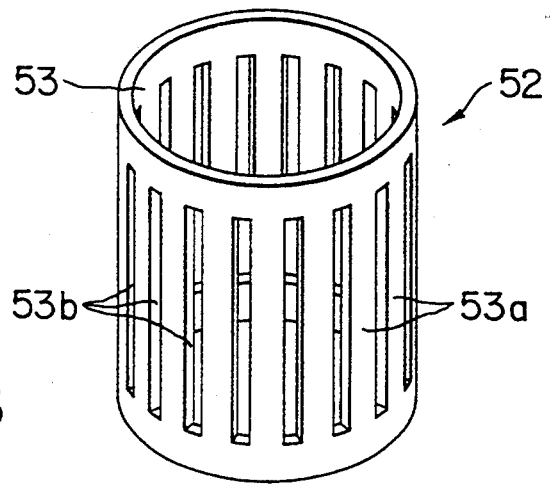
FIG. 6 is a perspective view showing a cylindrical coding body incorporated in the second and third embodiments of the present invention.

Further, a cylindrical coding body 52 is fitted to the inner wall of the cylindrical liner tube 15 in such a way as to enclose the plane reflecting mirror 51. The cylindrical coding body 52 has a signal generating surface 53 on the inner surface of which reflection portions 53a and non-reflection portions 53b are formed alternately and repeatedly, as shown in FIG. 6.

The functional operation of this second embodiment will be described hereinbelow.

A light beam 55 emitted from the end surface 29 of the optical fiber 28 is reflected by the plane reflecting mirror 51, irradiated upon the signal generating surface 53, and reflected by the signal generating surface 53 to generate an optical signal. The generated optical signal is reflected again by the plane reflecting mirror 51, guided into the end surface 29 of the optical fiber 28, and then transmitted to the light emitting and receiving apparatus 30.

In this embodiment, since the cylindrical coding body 52 and the plane reflecting mirror 51 are provided, it is possible to construct the ultrasonic probe in such a simple structure that the end surface 29 of the optical fiber 28 is solely arranged in the vicinity of the axial center of the tube 12.

Figure 7:
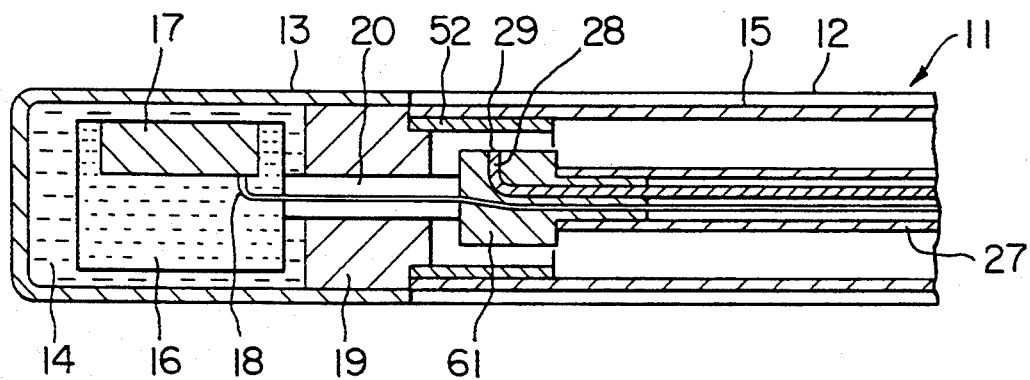
FIG. 7 is a cross-sectional view showing the end portion of a third embodiment of the ultrasonic probe according to the present invention.

A third embodiment of the present invention will be described hereinbelow with reference to FIG. 7.

In this embodiment, the cylindrical coding body 52 is fitted to an inner wall of the cylindrical liner tube 15. The optical fiber 28 is disposed so as to be passed through the flexible axle 27 and an optical fiber scanning member 61 attached to the end portion of the flexible axle 27. Further, the optical fiber 28 is bent radially outward at an angle of about 90 degrees in the vicinity of the end portion of the optical fiber scanning member 61 in such a way that the end surface 29 of the optical fiber 28 is opposed to the signal generating surface 53 of the cylindrical coding body 52 at the side portion of the optical fiber scanning member 61.

According to the construction of this third embodiment, since the cylindrical coding body 52 is provided and further the end surface 29 of the optical fiber 28 is disposed so as to be opposed to the signal generating surface 53 of the cylindrical coding body 52, it is possible to construct the ultrasonic probe in such a simple structure that the end surface 29 of the optical fiber 28 is solely located in the vicinity of the axial center of the tube 12 without use of any plane reflecting mirror 51.

What is claimed is:

1. An ultrasonic probe for observing an object to be observed by emitting an ultrasonic wave to the object and detecting another ultrasonic wave reflected from the object, which comprises:

a flexible tube;

an ultrasonic transducer disposed within said tube rotatably about an axial center of said tube; and a rotational information detecting apparatus for detecting rotational information of said ultrasonic transducer, including:

signal generating means disposed within said tube coaxially with respect to the axial center of said tube and having reflecting portions and non-reflecting portions formed alternately and repeatedly;

at least one optical fiber arranged along and in the vicinity of the axial center of said tube, for guiding a light beam to be irradiated upon said signal generating means from an end surface of said optical fiber and for receiving and guiding an optical signal reflected from said signal generating means at the end surface thereof; and optical signal detecting means for detecting the rotational information on the basis of the optical signal guided through said optical fiber.

2. The ultrasonic probe of claim 1, wherein said signal generating means is formed on a disk disposed coaxially with said tube.

3. The ultrasonic probe of claim 1, wherein said signal generating means is formed on an inner surface of a cylinder disposed coaxially with said tube and further comprises a reflecting mirror disposed at a position opposite to the end surface of said optical fiber so as to be rotatable together with said optical fiber, for emitting the light beam to said signal generating means and receiving the optical signal reflected therefrom.

4. The ultrasonic probe of claim 1, wherein said signal generating means is formed on an inner surface of a cylinder disposed coaxially with said tube, and said optical fiber is bent in the vicinity of the axial center of said tube in such a way that the end surface of said optical fiber is opposed to said signal generating means.

5. The ultrasonic probe of claim 1, wherein the light beam and the optical signal are both guided through said same optical fiber.

6. The ultrasonic probe of claim 1, wherein said optical signal detecting means detects the optical signal by separating polarized light of the optical signal from polarized light of the light beam.

7. An ultrasonic probe for observing an object to be observed by emitting an ultrasonic wave to the object and detecting another ultrasonic wave reflected from the object, which comprises:

a flexible tube;

an ultrasonic transducer disposed within said tube rotatably about an axial center of said tube; and a rotational information detecting apparatus for detecting rotational information of said ultrasonic transducer, including:

signal generating means disposed within said tube coaxially with respect to the axial center of said tube and having reflecting portions and non-reflecting portions formed alternately and repeatedly;

at least one optical fiber arranged along and in the vicinity of the axial center of said tube, for guiding a light beam to be irradiated upon said signal generating means from an end surface of said optical fiber and for receiving and guiding an optical signal reflected from said signal generating means at the end surface thereof, wherein light emitted from the end surface of said optical fiber is directed radially outward away from the vicinity of the axial center of said tube so as to be opposed to said signal generating means; and optical signal detecting means for detecting the rotational information on the basis of the optical signal guided through said optical fiber.

8. The ultrasonic probe of claim 7, wherein said signal generating means is formed on a disk disposed coaxially with said tube.

9. The ultrasonic probe of claim 7, wherein said signal generating means is formed on an inner surface of a cylinder disposed coaxially with said tube and further comprises a reflecting mirror disposed at a position opposite to the end surface of said optical fiber so as to be rotatable together with said optical fiber, for emitting the light beam to said signal generating means and receiving the optical signal reflected therefrom.

10. The ultrasonic probe of claim 7, wherein said signal generating means is formed on an inner surface of a cylinder disposed coaxially with said tube, and said optical fiber is bent in the vicinity of the axial center of said tube in such a way that the end surface of said optical fiber is opposed to said signal generating means.

11. The ultrasonic probe of claim 7, wherein the light beam and the optical signal are both guided through said same optical fiber.

12. The ultrasonic probe of claim 7, wherein said optical signal detecting means detects the optical signal by separating polarized light of the optical signal from polarized light of the light beam.

* * * * *